(12) United States Patent
Mohapatra et al.

(10) Patent No.: US 10,045,717 B2
(45) Date of Patent: Aug. 14, 2018

(54) WIFI-BASED PERSON-IDENTIFICATION TECHNIQUE FOR USE IN SMART SPACES

(71) Applicant: The Regents of the University of California, Oakland, CA (US)

(72) Inventors: Prasant Mohapatra, Davis, CA (US); Parth H. Pathak, Davis, CA (US); Yunze Zeng, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/611,545

(22) Filed: Jun. 1, 2017

(65) Prior Publication Data
US 2017/0354349 A1 Dec. 14, 2017

Related U.S. Application Data

(60) Provisional application No. 62/348,723, filed on Jun. 10, 2016.

(51) Int. Cl.
| | |
|---|---|
| G05B 19/00 | (2006.01) |
| A61B 5/117 | (2016.01) |
| H04B 7/06 | (2006.01) |
| H04L 29/08 | (2006.01) |
| H04L 27/26 | (2006.01) |
| A61B 5/00 | (2006.01) |
| A61B 5/11 | (2006.01) |
| H04W 84/12 | (2009.01) |

(52) U.S. Cl.
CPC ............ *A61B 5/117* (2013.01); *A61B 5/0022* (2013.01); *A61B 5/112* (2013.01); *A61B 5/7203* (2013.01); *A61B 5/7257* (2013.01); *H04B 7/0626* (2013.01); *H04L 27/265* (2013.01); *H04L 67/22* (2013.01); *H04L 67/306* (2013.01); *H04L 27/261* (2013.01); *H04L 27/2671* (2013.01); *H04L 27/2672* (2013.01); *H04W 84/12* (2013.01)

(58) Field of Classification Search
CPC ...................................................... A61B 5/117
USPC ...................................................... 340/5.82
See application file for complete search history.

(56) References Cited

U.S. PATENT DOCUMENTS

| | | | | |
|---|---|---|---|---|
| 2007/0058789 | A1* | 3/2007 | Lim | H04W 76/025 379/88.17 |
| 2009/0046011 | A1* | 2/2009 | Tung | H04B 7/0417 342/377 |
| 2012/0177194 | A1* | 7/2012 | Yoon | H04W 8/06 379/212.01 |
| 2015/0043372 | A1* | 2/2015 | Nagata | H04L 5/0057 370/252 |
| 2015/0282133 | A1* | 10/2015 | Kakishima | H04J 11/00 370/329 |

(Continued)

*Primary Examiner* — Santiago Garcia
(74) *Attorney, Agent, or Firm* — Park, Vaughan, Fleming & Dowler LLP

(57) ABSTRACT

The disclosed embodiments relate to the design of a system that identifies a person. During operation, the system receives channel state information (CSI) for a set of orthogonal frequency division modulation (OFDM) subcarriers while the person moves in a region that includes two or more nodes that use the set of OFDM subcarriers to communicate with one another. Next, the system analyzes the CSI to obtain an analysis result. The system then determines the identity of the person based on the analysis result.

30 Claims, 11 Drawing Sheets

(56) References Cited

U.S. PATENT DOCUMENTS

2016/0277529 A1\* 9/2016 Chen ................ H04L 67/306
2017/0310375 A1\* 10/2017 Kim ................ H04L 1/0026

\* cited by examiner

WIFI-BASED PERSON-IDENTIFICATION TECHNIQUE FOR USE IN SMART SPACES

CROSS-REFERENCE TO RELATED APPLICATION

This application claims the benefit of U.S. Provisional Application Ser. No. 62/348,723, entitled "Method and System for Identifying a User," by inventors Prasant Mohapatra, Parth H. Pathak and Yunze Zeng, filed on 10 Jun. 2016, the contents of which are incorporated by reference herein.

BACKGROUND

Field

The disclosed embodiments generally relate to techniques for automatically identifying people. More specifically, the disclosed embodiments relate to a person-identification technique that uses WiFi® signals to identify a person within a smart indoor space.

Related Art

There has been an increasing interest in offloading the functionality of user's smart devices to the infrastructure surrounding the user. Embedding sensing, computation and communication capabilities in the environment, such as a home or an office, can allow a person to be truly "device-free," while still receiving the same services that are otherwise available through portable/wearable devices like smartphones. Such intelligent environments are often referred to as "smart spaces." Numerous applications can be enabled with the realization of smart spaces. However, many of these applications require a person to carry a portable electronic device, such as a smartphone. For example, the process of counting the number of steps walked by a person requires the person to constantly carry a device, such as a smartphone or fitness band, at all times even while at home. Similarly, tracking sleep behavior requires a person to wear a sleep-tracking device even during sleep. The need to carry or wear a device creates a great deal of discomfort for the user and also inaccuracy in associated measurements when the user does not wear the device as suggested. With the emergence of smart spaces, such sensing and activity-tracking functionality can be performed by the environment (home or office) itself, relieving people of the need to constantly wear smart devices.

However, enormous challenges stand in the way of truly realizing smart spaces. Tracking a person's actions in a smart space requires sensing the person's actions without any physical interaction with the person. Moreover, the task of identifying a person is a prerequisite for activity recognition, because without knowing the identity of a person, it is not possible to associate a sensed activity with the person. For example, if a system can identify a person who is in the home, a detected activity, such as cooking, can be associated with that person. In general, the ability to identify a person can facilitate many applications in smart spaces. For example, when a smart home detects that a specific one of five family members has entered the home, it can use the identity of the family member to trigger person-specific customization, such as adjusting room temperature according to preferences of the person, providing a content recommendation tailored to the person on a television, and starting a coffee machine for the person if the person typically drinks coffee. It can also facilitate Internet-of-Things (IoT) applications that might be otherwise infeasible without knowing the person's identity.

Existing techniques for identifying a person rely on the person performing an affirmative action, such as swiping an ID card or using a thumb-print scanner. However, it is inconvenient for a person to have to perform affirmative actions to identify themselves every time they enter a smart space. It is also possible to use a camera and an associated image-processing system to recognize a person. However, the use of cameras in homes and offices creates significant privacy concerns.

Hence, what is needed is a technique for automatically identifying a person in a smart space without the drawbacks of the above-described existing techniques.

SUMMARY

The disclosed embodiments relate to the design of a system that identifies a person. During operation, the system receives channel state information (CSI) for a set of orthogonal frequency division modulation (OFDM) subcarriers while the person moves in a region that includes two or more nodes that use the set of OFDM subcarriers to communicate with one another. Next, the system analyzes the CSI to obtain an analysis result. The system then determines the identity of the person based on the analysis result.

In some embodiments, the CSI includes amplitude and phase information for each of the set of OFDM subcarriers.

In some embodiments, the two or more communication nodes are WiFi-capable nodes, and the CSI is defined by a WiFi standard, such as IEEE 802.11n or 802.11ac.

In some embodiments, prior to analyzing the CSI, the system performs a preprocessing operation on the CSI, wherein the preprocessing operation: removes noise caused by distant multipath signal propagation; and removes high-frequency noise.

In some embodiments, while analyzing the CSI, the system performs a walking-detection operation to determine whether the person is walking prior to performing a gait-analysis operation. During this walking-detection operation, the system: computes a motion-energy metric based on normalized Fast-Fourier Transform (FFT) components of the CSI; and determines whether the person is walking based on the motion-energy metric.

In some embodiments, while analyzing the CSI, the system performs a gait-analysis operation. During this gait-analysis operation, the system calculates features of one or more steps of the person based on the CSI; calculates features of a walk of the person based on the CSI; and determines a gait profile of the person based on the features of the steps and the walk of the person.

In some embodiments, while calculating the features of the steps of the person, the system: performs a step-cycle construction operation, which uses a peak-valley detection technique based on amplitude of the CSI to divide the CSI into step cycles; uses a band-pass filter to remove high-frequency noise from the CSI; and calculates time-domain features of the CSI for each step cycle.

In some embodiments, while calculating the features of the walk of the person, the system calculates features over a walk segment, which includes multiple step cycles, wherein calculated features include: frequency-domain features computed across all frequency bands of the CSI; and time-domain features computed across an activity frequency band from 0.3 to 2 Hz of the CSI.

In some embodiments, while determining the identity of the person based on the analysis result, the system uses a decision-tree classifier to classify the gait profile of the person as belonging to a specific person in a set of persons.

In some embodiments, prior to receiving the CSI, the system performs a training operation, which uses a set of gait profiles for each of the set of persons to train the decision-tree classifier.

Figure 1:
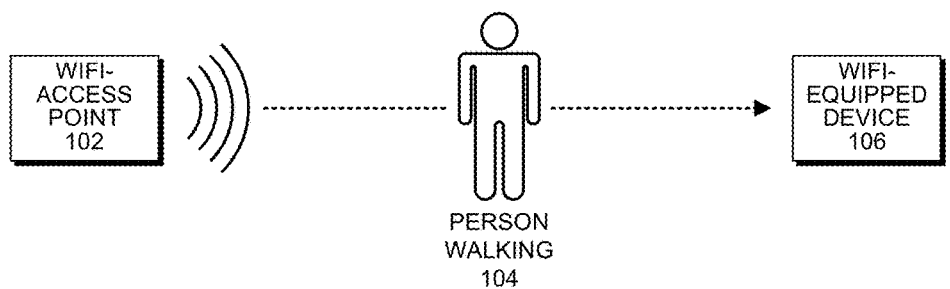
FIG. 1 illustrates a person walking between a WiFi access point (AP) and a WiFi-equipped device in accordance with the disclosed embodiments.

Table I lists exemplary time-domain and frequency-domain features in accordance with the disclosed embodiments.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), flash drives and other portable drives, or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

Overview

The disclosed embodiments provide a technique for using WiFi signals to identify a specific person from a group of n known people. This technique is useful in smart homes and offices where the person can be identified from n known people sharing the home or office. For example, this technique is applicable to a typical house or apartment complex that is shared by 4-5 family members, or an office that is shared by 6-7 people. In both cases, it is reasonable to assume that there exists an active WiFi connection.

However, person identification using WiFi is a challenging problem. One solution is to analyze the WiFi signals reflected from a person's body. Assuming that the person is stationary (e.g., standing without any movement), the received signal might have different signatures for different people depending on the person's height, weight and body mass. The problem with this approach is that it is extremely difficult to isolate the signal that is reflected from a person's body because indoor WiFi signal propagation is dominated by distant multipath propagation effects caused by multiple reflected signal paths.

The disclosed embodiments make use of a novel technique for using WiFi signals to identify a person. In particular, this technique uses WiFi channel state information (CSI) to identify a person's walking gait. Similar to accelerometer-based gait analysis, the system analyzes CSI-based gait information for different people to first identify steps of a person, and then distinctly identify the person. This makes it possible to identify a person from a small group of people without requiring the person to carry a mobile device, or proactively perform an action to be identified.

Note that this technique is particularly well-suited for person identification in smart spaces because it does not require a person to carry any device (such as a smartphone) for identification. This is especially important in indoor environments, because a person might not carry the smartphone with her at all times. Moreover, unlike face- or fingerprint-recognition techniques, which involve deploying dedicated hardware, this technique uses the existing WiFi infrastructure for identification. It also provides better privacy than identification techniques that rely on audio or video monitoring.

Details

Assume that there exist two stationary endpoints in a room of the home or the office in which the system is deployed, and these endpoints communicate with each other to collect the WiFi CSI. For example, referring to FIG. 1, one endpoint can be a WiFi access point (AP) 102 and the other can be any WiFi-equipped device 106 such as a desktop computer or a smart TV. The two endpoints are used to collect the CSI data, and the system is only required to be operating on one of the endpoints (say the AP). Also assume that a person 104 (not equipped with any device) starts walking in the room, preferably in a direction along a line between the two endpoints.

Figure 2:
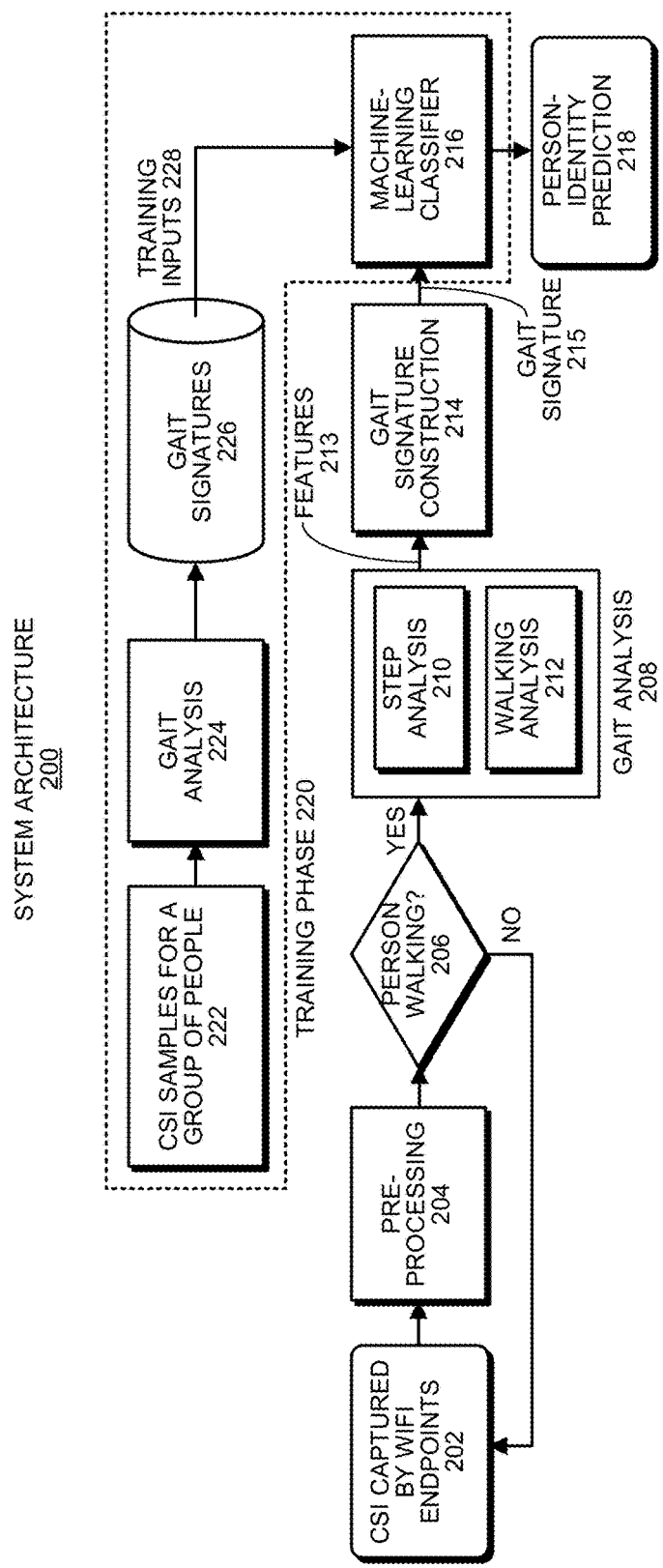
FIG. 2 illustrates an architecture for a WiFi-based person-identification system in accordance with the disclosed embodiments.

A high-level system architecture 200 for the person-identification system appears in the block diagram illustrated in FIG. 2. During operation, the WiFi endpoints illustrated in FIG. 1 monitor CSI, and the captured CSI 202 is fed through a preprocessing module 204 to remove noise caused by distant multipath signal propagation and also to remove other high-frequency noise. At the same time, the collected CSI samples are constantly analyzed to determine whether the person is walking (block 206). If the system does not detect that a person is not walking (NO at box 206), the system returns to box 202 to obtain more captured CSI. On the other hand, if the system detects that a person is walking (YES at box 206), the CSI samples are fed into a gait-analysis module 208. This gait-analysis module 208 includes two parts: (1) a step-analysis module 210, wherein the step cycle is constructed from the CSI data; and (2) a walking-analysis module 212 that analyzes the overall walking behavior of the person in a walk segment comprising multiple steps. Note that this walking analysis provides information on various body movements that can differ from person to person.

The characteristics of the person's step and walk are then extracted in the form of features 213. These features 213 feed into a gait signature construction module 214, which produces a gait signature 215. Gait signature 215 is then fed into a machine-learning classifier 216, which uses a machine-model that was trained on walk signatures for a group of people to classify signature 215 as belonging to a specific person in the group of people. This enables machine-learning classifier 216 to produce a person-identify prediction 218.

Referring to the top of FIG. 2, during a training phase 220, each person in a group of people who would like to be identified walks along a pre-determined path between two WiFi endpoints a fixed number of times, and the resulting CSI samples for the group of people 222 are collected. CSI samples 222 are then fed into a gait-analysis module 224, which extracts gait signatures 226 for each person in the group of people. Next, gait signatures 226 are used as training inputs 228 for machine-learning classifier 216 during subsequent training operations.

The above-described system operates with a number of assumptions and limitations. The system works best when the person's walking path is along a straight line. This is because CSI variations that arise when a person turns while walking make it extremely difficult to identify the steps and gait. However, this constraint does not reduce the usability of the system significantly. In a home or an office, a straight walkway such as a corridor or a hallway can be chosen for sampling the walking. In fact, choosing a walkway that leads into a home or an office works well because a person can be identified as the person enters the home or office. Additionally, the system cannot be used to track the location of a person because the identification is only triggered when the person enters or leaves the room. The system is also designed to identify a single person who is located in the room, so the system can associate a certain activity detected by WiFi signals with that person. However, note that the system can remove the impact of another person's presence outside the room by using various distant multipath propagation noise removal techniques as described in more detail below.

Empirical Results

This section presents empirical results indicating the feasibility of performing WiFi-based person identification based on measureable characteristics of the person's gait. The first challenge of designing this system is to determine when there is a noticeable pattern in the observed CSI while a person is walking.

Figure 3A:
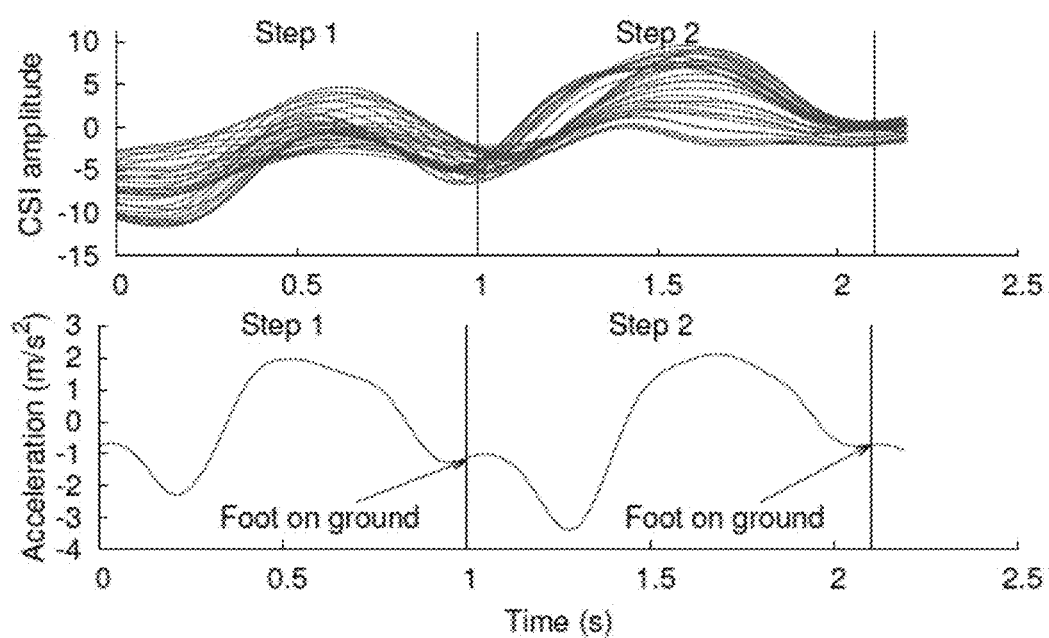
FIG. 3A illustrates a comparison of CSI amplitude and accelerometer readings in accordance with the disclosed embodiments.

However, note that simply detecting whether a person is walking or not is not sufficient to identify a specific person. This more-complicated person-identification process is performed by analyzing a person's gait. To demonstrate whether a person's gait can be identified using CSI, experiments were conducted where a person walks along a straight line in a room between two WiFi endpoints and associated CSI is collected. For generating a more-accurate indicator of gait, the person also carries a smartphone. For example, FIG. 3A illustrates exemplary synchronized CSI and accelerometer data for a person's walk. For the CSI data, the amplitude of 30 subcarriers was plotted for one spatial stream, and for accelerometer data, the acceleration values for the x-axis of the accelerometer were plotted. Note that the raw CSI data was also preprocessed to remove various types of noise as is discussed in more detail below.

It is observed from FIG. 3A that step cycles can be extracted from the CSI data. Moreover, the steps cycles observed in the CSI data follow a similar pattern of alternating peaks and valleys. However, unlike the accelerometer observations, the step cycles detected by CSI are less pronounced. Nevertheless, empirical results demonstrate that this CSI-based gait information is rich enough for person identification. Note that because CSI-based gait information is observed by nearby WiFi devices, and not by a device worn on the person's body, it depends on location-specific multipath propagation effects. This means that the gait pattern varies at different locations as the person walks around a room. Solutions to this issue are discussed in more detail below.

Figure 3B:
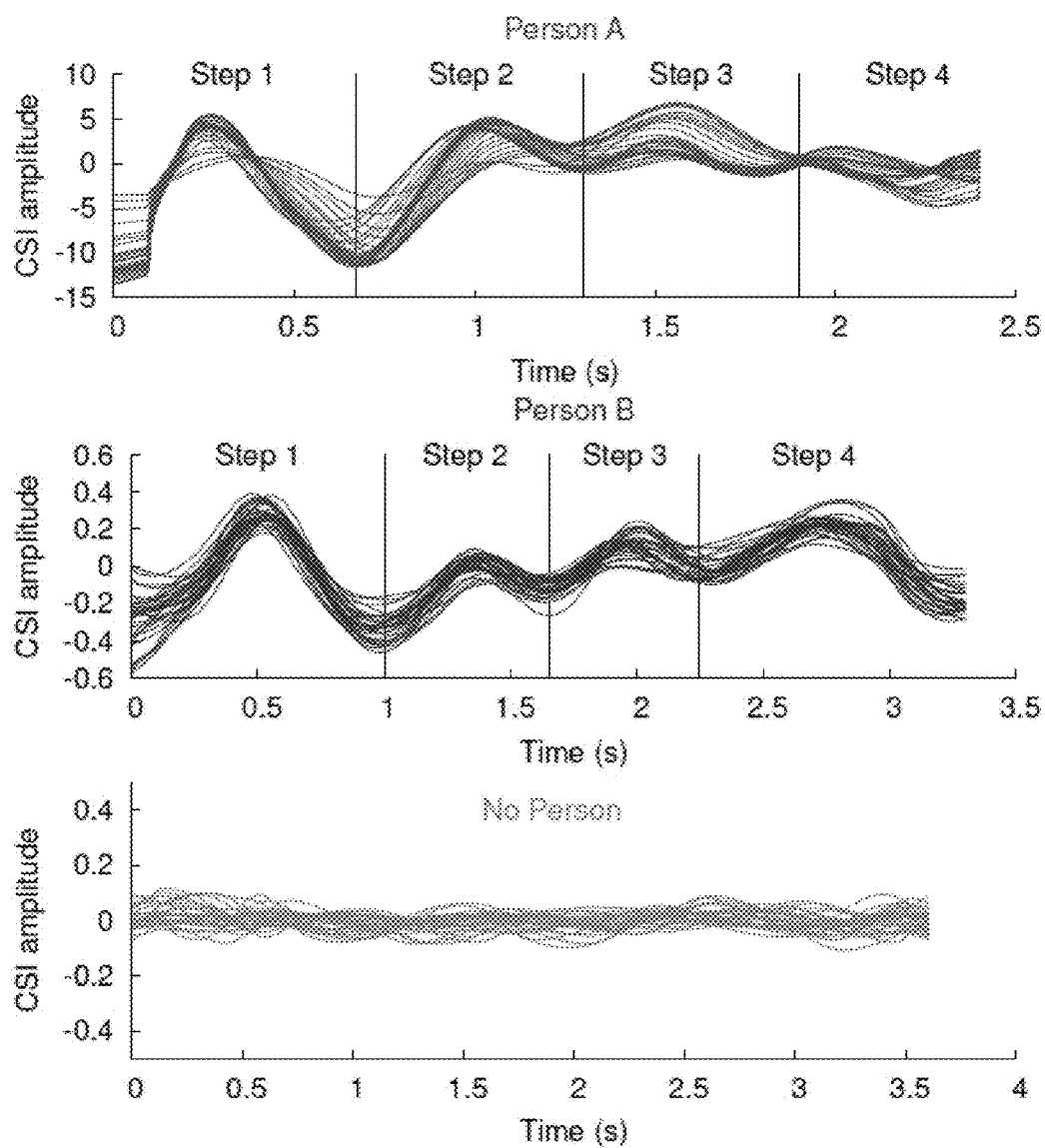
FIG. 3B illustrates a comparison of the CSI-based gait of two people and a static environment profile in accordance with the disclosed embodiments.

Although gait information can be obtained from the CSI, it is not clear whether such information is sufficient to uniquely identify a person from a group of people. To investigate this, an experiment was performed where two people walk in a room along the same path and the system captures the resulting CSI data. FIG. 3B shows the CSI data for four initial steps while two people are walking separately. Note that FIG. 3B also illustrates the static environment CSI profile where there is no person walking in the room. By visual inspection, it can be seen that differences between the shape of the steps for the two people and the static profile are quite clear. Also, the step lengths are different for the two people. This visually observed difference and many other underlying differences can be used to build a unique gait profile for each person, wherein the gait profile can be used to subsequently identify the person.

Figure 4:
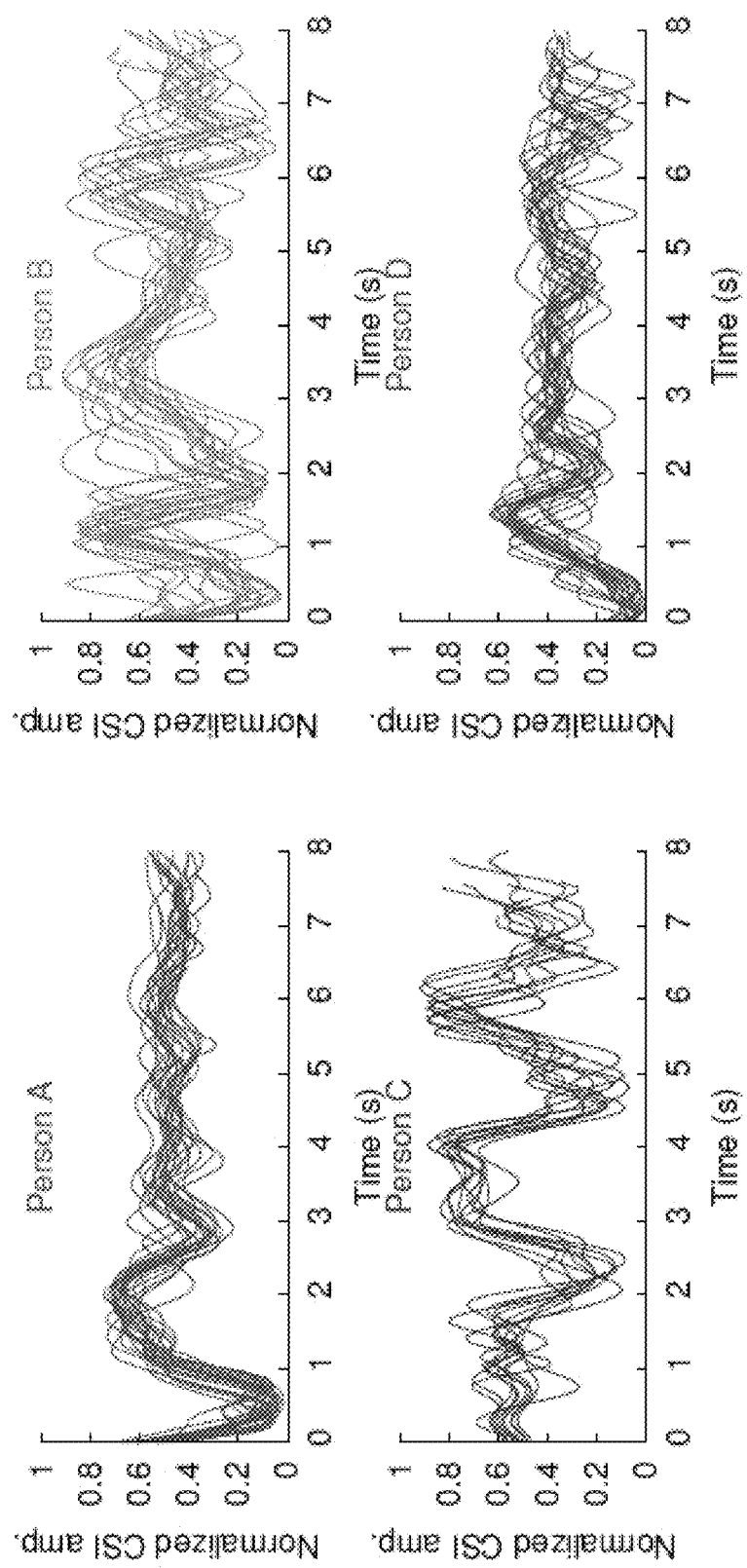
FIG. 4 illustrates a comparison of the CSI-based gait for four different people in accordance with the disclosed embodiments.

Another question to investigate is whether the CSI-based gait for a person remains the same over time for the same location (e.g., the same room). Hence, if a person's CSI-based gait is learned at one time, can the same gait be used to identify the same person at a different time? To address this question, four different people were asked to walk one after the other to collect their gait information for 20 rounds. To examine the consistency over time, the rounds were separated by 10 minutes. FIG. 4 presents a corresponding plot of the mean CSI amplitude across all subcarriers of each round of the four different people. Note that for any given person, the CSI-based gait remains similar between each round over nearly 2 hours of measurements.

The above-described empirical results show that CSI-based gait information for a person is more or less consistent over time, and it is sufficiently different for different people to facilitate identification of a specific person. Hence, the empirical results indicate that it should be possible to construct a person-identification system based on a CSI-based gait.

CSI Preprocessing

This section describes additional details about the preprocessing operation performed by preprocessing module 204 illustrated in FIG. 2. Note that existing WiFi standards, such as 802.11n and 802.11ac, use Orthogonal Frequency Division Modulation (OFDM) for their physical layer. In OFDM, the channel is divided into multiple subcarriers and the data is transmitted over the subcarriers using the same modulation and coding scheme. The CSI information represents the amplitude and phase information of the OFDM subcarriers. More specifically, it provides a complex-number matrix that shows the Channel Frequency Response (CFR) of each individual subcarrier for all spatial streams. Unfortunately, the raw CSI data includes noise that can possibly interfere with person-identification operations; this includes noise caused by distant multipath signal propagation and other high-frequency noise.

Figure 5B:
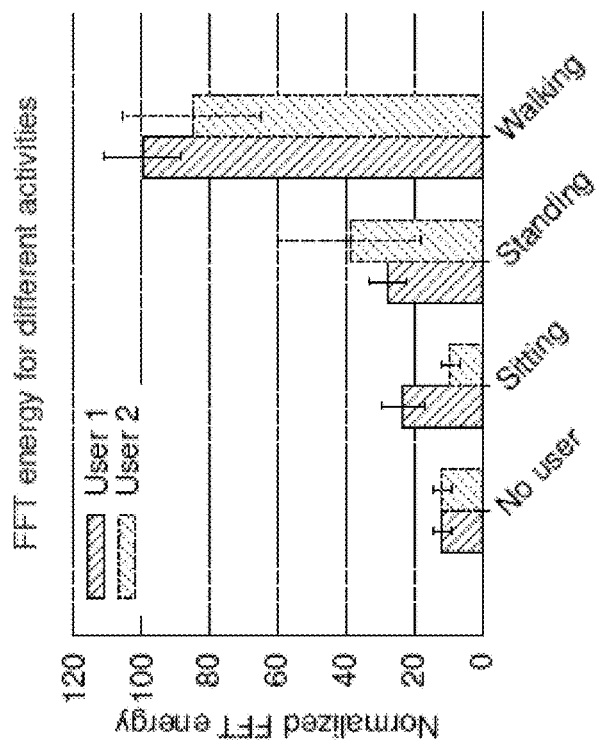
FIG. 5B illustrates a comparison of motion energy for different activities in accordance with the disclosed embodiments.
Figure 5A:
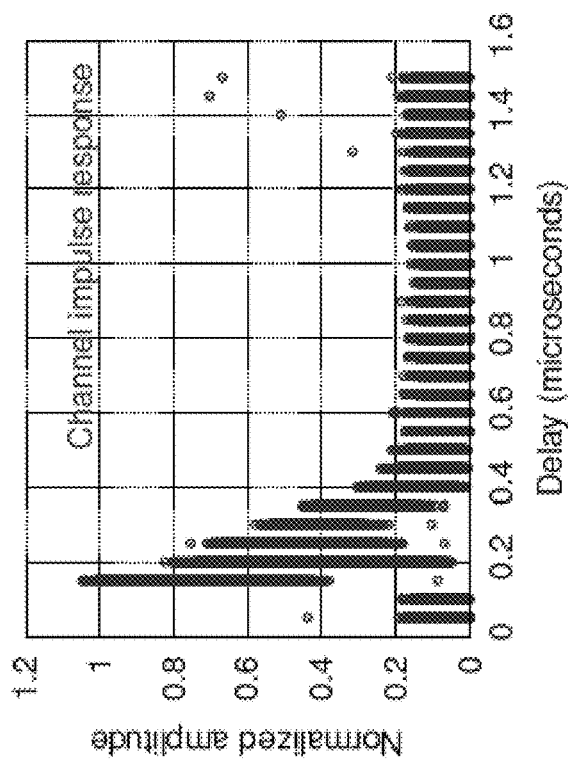
FIG. 5A illustrates a channel-impulse response for a distant multipath propagation in accordance with the disclosed embodiments.

Distant multipath signal propagation noise is caused by reception of a strong signal due to reflection from a distant object or person. For example, in the gait-related person-identification system described above, such reflections can be due to the person moving far away from the room where the CSI is collected. This distant multipath noise can cause the observed CSI profile to vary in a non-deterministic manner, which can adversely affect the gait analysis. This problem can be addressed by removing the distant multipath noise from the CSI data. Note that the CSI contains CFR data for 30 subcarriers, which include the distant multipath noise. To remove this distant multipath noise, the CFR data can be converted into Channel Impulse Response (CIR) data, which provides a delay profile of the signal reception. An exemplary CIR is shown in FIG. 5A, which illustrates distant multipath components after the delay of 1 microsecond. Distant multipath components having a delay greater than 0.5 microseconds are removed, and the OR data is converted back into CFR data using an FFT (Fast Fourier Transform). Note that this 0.5 microsecond threshold is chosen based on the multipath delay characterization provided by empirical measurements. This distant multipath removal allows us to focus on the reflected paths within a room, which are required for fine-grained analysis of a person's gait.

The system also removes other high-frequency noise from the time-domain CSI signal. Note that the walking activity of a person typically exhibits energy in the 0.3 Hz to 2 Hz frequency band. This energy can be caused by arm and leg movements while walking, which are known to happen at no more than 2 Hz. In order to separate the step cycles from the time-series CSI data, the system applies a Butterworth bandpass filter with cutoff frequency of 0.3 Hz to 2 Hz to the CSI data, wherein such filtering also removes the static DC component.

Note that this high-frequency filtering is only useful for step analysis, which identifies step cycles and performs step-shape analysis. The system also performs a walk-analysis operation over an entire walk segment, which comprises multiple step cycles. However, this walk analysis involves studying the movement of body parts, which may happen at a faster rate than 2 Hz. Hence, the system separately studies different frequency bands (up to 10 Hz) for walk-analysis purposes.

Walking Detection

As shown in FIG. 2, the first step in identifying a person using CSI-based gait analysis is to detect whether a person is walking or not. This section describes how to detect a walking activity using CSI data, and also how to distinguish it from other indoor activities such as standing, sitting, typing, etc. Accurately detecting the walking activity ensures that the gait-based person analysis is only initiated in cases where a person is found to be walking.

The below-described approach, which distinguishes various activities from the CSI data, stems from accelerometer-based and gyroscope-based activity-recognition techniques. Previous research has shown that different human activities can be identified using frequency-domain analysis of accelerometer data (or gyroscope data) of a person's movements because typical indoor activities such as sleeping, standing, sitting, and walking exhibit different characteristics in the frequency domain. These activities can be categorized as low-intensity or moderate-intensity activities. (See [Mung2008] E. Munguia Tapia, "Using machine learning for real-time activity recognition and estimation of energy expenditure," Ph.D. dissertation, MIT, 2008.) Because a walking-detection operation needs to be performed constantly by the system, the walking-detection technique should ideally be simple and efficient. Examining simple features in the frequency domain works well for the purpose. (Note that a smart space environment allows us to exclude high-intensity outdoor activities, such as driving and playing sports, which in turn simplifies how the system determines whether a person is walking or not.)

Figure 6:
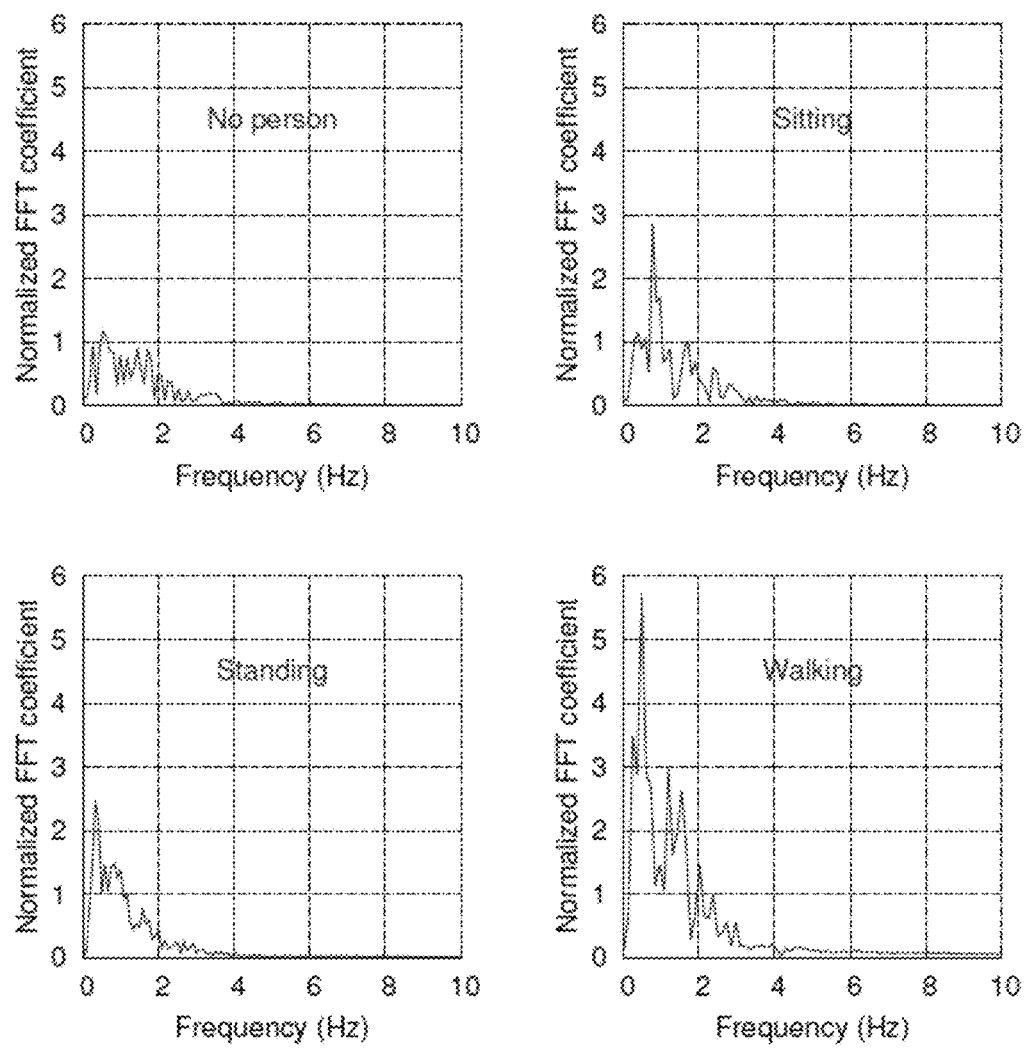
FIG. 6 presents a comparison of FFT coefficients for different activities in accordance with the disclosed embodiments.

To verify that frequency-domain properties of different activities are also observable in the CSI data, experiments were performed in situations where: (1) no person was in the room; (2) a person was sitting and performing routine activities such as typing and moving objects on a desk; (3) a person was standing (without taking steps) using her phone and writing on a whiteboard; and (4) a person was walking. FIG. 6 shows the coefficients of a resulting FFT profile for these four activities (without the DC component) as observed in the CSI data. For the case where no person was in the room, very low amplitudes for FFT coefficients were observed in the low frequency band. In comparison, sitting and standing exhibited higher amplitude values (more intensity) for the same frequencies. However, for the walking activity, the observed amplitudes in the 0.3-2 Hz range are noticeably higher. This is expected because the movement of legs and arms while walking is known to have frequencies within this range.

To represent the FFT profile of different activities, the system uses a metric, which is referred as "motion energy" [Mung2008]. The motion energy (or simply energy) can be calculated as follows:

$$\text{Energy} = \sum_{i=1}^{window\_length/2} magnitude^2. \quad (1)$$

where the magnitude values are normalized Fast Fourier Transform (FFT) coefficients calculated over a time window. FIG. 5B shows the observed energy for the four activities for two different people. Because the energy observed during the walking is much higher than during sitting or standing, the system can use the motion energy to determine whether a person is walking or not.

Gait Analysis

As illustrated in FIG. 2, the CSI-based gait analysis involves both: (1) step analysis; and (2) walk analysis. This section first describes the features used for both types of analyses, and then explains how they are used for the step analysis and walk analysis operations to construct a gait profile, which is used for person identification.

Constructing CSI Features

Designing a feature space that can capture a person's walking gait is challenging because the CSI includes amplitude and phase values for each of the subcarriers and spatial streams, which creates a large amount of data. Hence, dimensionality reduction is necessary for a tractable analysis. This work primarily focuses on one spatial stream because of significant similarities among the data from multiple spatial streams, which allows one stream to be analyzed to lower the computational cost. Let $v_t = \{c_1, c_2, \ldots, c_s\}$ be the CFR vector for s subcarriers at time t. The system appends additional statistics to $v_t$ to generate a vector $v_t^*$, which includes $v_t$, and the maximum, minimum, mean, median, standard deviation, skewness and kurtosis of $v_t$. These statistics capture the shape (e.g., peakedness, symmetry, and variation) of instantaneous distribution of CFR for all subcarriers. This process is repeated for each new sample of CSI data for the remainder of the feature calculation.

The features are calculated over a time window, where the time window can span a single step or an entire walk segment. Table I lists the time-domain and frequency-domain features that can be calculated for the time window. For a window of size T, the features in Table I are calculated for each subcarrier and its statistics are included in $v_t^*$ for all t in T. Note that these features enable detailed time and frequency analysis of CSI data for the time window. The frequency domain features, such as entropy and energy, are included because they profile the walking activity inside the time window with high accuracy. Note that the choice of time window depends on whether the system is analyzing individual steps or an entire walk segment. To evaluate the importance of these features for person identification, Information Gain (IG) can be used as a metric. (See I. H. Witten and E. Frank, *Data Mining: Practical machine learning tools and techniques*. Morgan Kaufmann, 2005.)

TABLE I

Time domain:

Minimum (min); min10th; maximum (max); max90th; mean; variance (var); Standard deviation (std); range.
CV: ratio of Standard deviation and mean times 100; skewness ($3^{rd}$ moment); kurtosis (4th moment).
First, second and third quartiles.
Inter Quartile Range (ICR): difference between the third and the first quartile.
Mean Crossing Rate (MCR): number of times the signal crosses the mean value)
Area under the signal curve (Area) and autocorrelation.

Frequency domain:

Energy: measure of total energy in all frequencies (as in Eq. 1).
Entropy: measures the impurity in the CSI signal.
DomFreqRatio: calculated as the ratio of highest magnitude FFT coefficient to sum of magnitude of all FFT coefficients.
FFTPeaks: 5 largest frequencies in the signal and their magnitude.

Figures 7A, 7B:
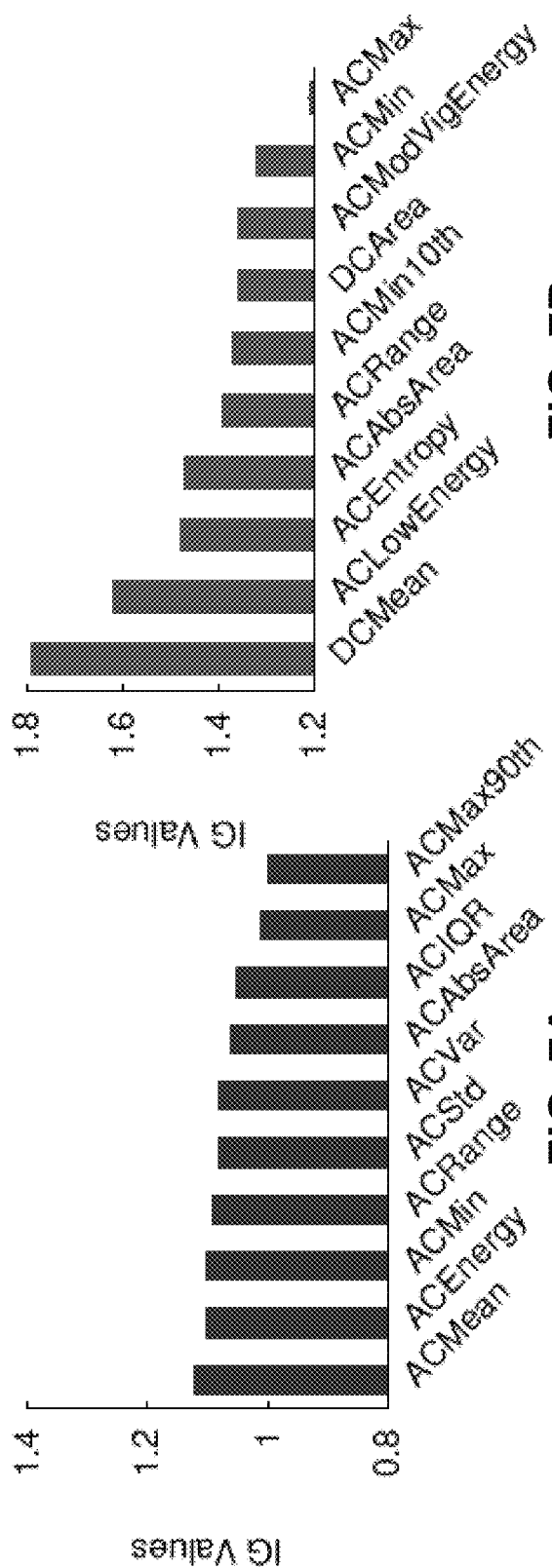
FIG. 7A illustrates information gain values for selected features during a step analysis in accordance with the disclosed embodiments.
FIG. 7B illustrates information gain values for selected features during a walk analysis in accordance with the disclosed embodiments.

FIG. 7A shows the top ten features used to conduct per-step analysis, and FIG. 7B shows the top ten features used to walking analysis. Note that the average IG value for the selected features for walking analysis in FIG. 7B is higher than for the selected features for per-step based analysis in FIG. 7A. Also note that the high-IG features for walking include many frequency-domain features. However, for per-step analysis, the high-IG features are mostly time-domain features.

Analyzing a Person's Steps

The step-analysis process evaluates how steps differ from person to person as observed by CSI. Previous research shows that the shape of the step varies noticeably for different people. This has led to the development of a number of person-authentication techniques where a smartphone's accelerometer signal is analyzed to differentiate among a group of people. The challenge with the use of CSI is that the shape of a typical step of a person is highly dependent on the static multipath configuration of the environment. Hence, the shape of a person's step changes at different locations in a room depending on the multipath characteristics of that location. When the person walks from one point to another point in the room, the shape of steps changes depending on the relative position of WiFi endpoints and multipath propagation effects.

Step-Cycle Construction: The step analysis process initially involves finding the step cycle of the first step. However, finding this step cycle is not trivial. Consider the case where the time-series CSI data starts from time $T_s$ and goes to time $T_e$. The system seeks to determine the step cycle of each step in the time period. However, the number of steps taken during this time period is unknown. One possible solution to this problem is to create step templates for different people from the training data and to compare them with CSI data in the ($T_e$-$T_s$) window using Dynamic Time Warping (DTW) to determine the step cycles. However, this requires an exhaustive brute-force analysis, because every person's step template has to be compared with the current window. Moreover, this type of brute-force analysis incurs a prohibitively large computational cost given that DTW requires solving an optimization problem with dynamic programming. Furthermore, because the step shape for each person varies at different locations along the walking path, this type of template-matching technique exhibits very low accuracy while constructing step cycles.

Instead of using DTW, the system uses a peak-valley detection technique for step-cycle construction. This peak-valley detection technique detects step cycles based on local minima and maxima of time-series data along with a significance constraint. (See R. Schneider, "Survey of peaks/ valleys identification in time series," 2011.) Using this technique, the system denotes the time from the start to the first valley to be the duration of the first step as is illustrated in FIG. 3A. Immediately after the system detects that a person is walking, the system starts detecting the step cycle. The system also sets up an expected step cycle time range from 0.8 s to 1.8 s. If the system detects a step cycle that is less than 0.8 s, the system will additionally include the next peak or valley in the step cycle. If the system detects a step cycle that is greater than 1.8 s, the system starts a new step-cycle detection. The duration of the first step is subsequently used to detect the rest of the step cycles. This assumes that the step duration does not vary significantly during the walk segment. This is a reasonable assumption because the system assumes that the person walks along a straight line path without any turns or breaks while the system gathers the CSI. Note that the peak-valley detection technique does not detect trivial peaks and valleys because the input CSI data is already filtered to remove high-frequency noise.

Figure 8B:
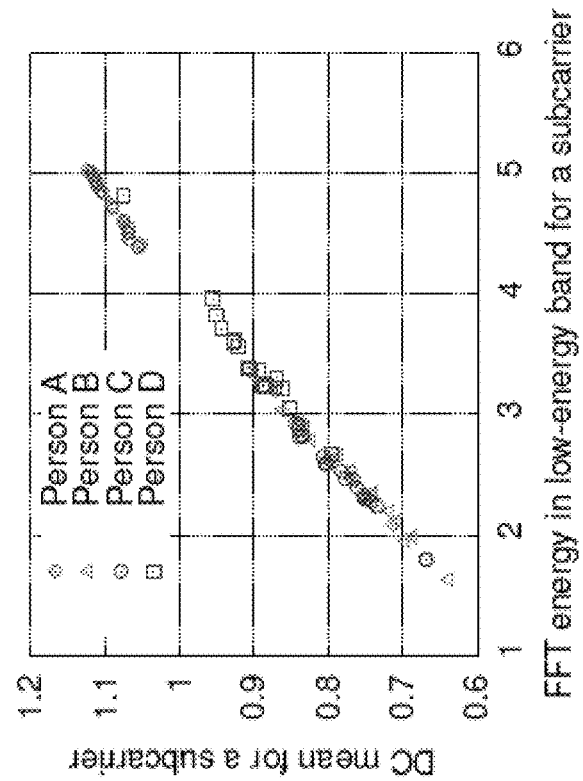
FIG. 8B illustrates selected features that are considered during a walk analysis in accordance with the disclosed embodiments.
Figure 8A:
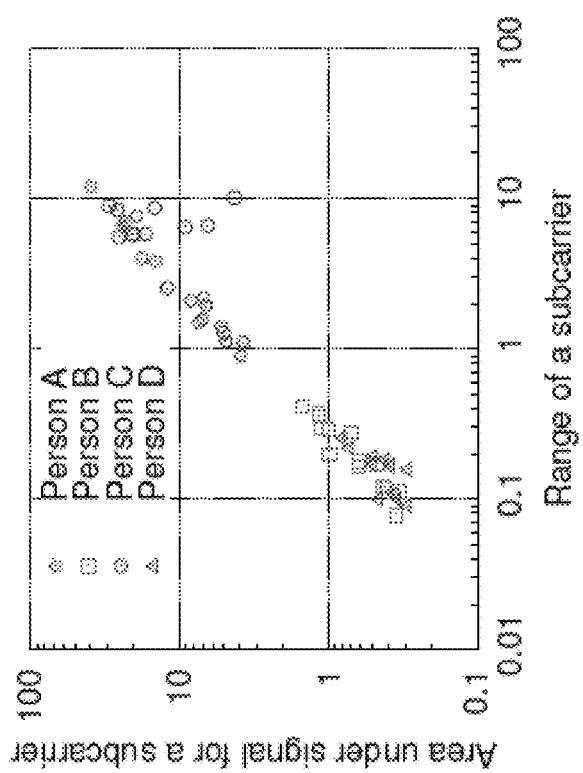
FIG. 8A illustrates selected features that are considered during a step analysis in accordance with the disclosed embodiments.

Per-Step Feature Calculation: After the step cycle of each step is determined from the input walking segment, the CSI data in the time window of each step is used to calculate step features. The system first applies a 0.3-2 Hz bandpass filter to the CSI to remove high-frequency noise, and then calculates the time domain features listed in Table I. Note that the system does not calculate frequency-domain features because they provide only a small amount of information within such a small time window. The time-domain features represent the shape of the person's steps in the form of statistics. Given that the shapes of different people's steps are likely to be different even at the same location, this allows the system to perform step-based person identification. FIG. 8A shows how two of the features (area under the curve and range) are different for the steps of different people. Note that these results are shown for one representative subcarrier only, which is not sufficient for person identification. However, all the features calculated for all subcarriers of the CSI data for a step are combined into a vector for the step, and this combined vector provides sufficient information to help in identifying the person.

Analyzing a Person's Walk

The step analysis process described above helps in identifying the typical pattern of each step of a person. However, it cannot capture the person's overall walking behavior, which changes on a time scale that is faster or slower than the step duration. For such analysis, the system performs frequency-domain analysis to obtain information about other characteristics, such as: the amount of energy in the walk segment across different steps; high-frequency movement such as movement of arms; and minor posture changes. Such characteristics, which are analyzed during the walk analysis, can also help the system to distinguish among different people when combined with the step analysis.

To perform the walk analysis, the system uses the CSI for each of the subcarriers to calculate the features presented in Table I for the entire walk segment. For calculation of frequency-domain features, the system first identifies the following three activity bands:

(1) a low-energy band from 0-0.7 Hz;
(2) an activity band from 0.3-2 Hz; and
(3) a high-energy band from 0.7-10 Hz.

The low-energy band has been found to be useful to profile slow-moving activities, such as a posture change. (It also includes the static DC component.) The activity band is of primary interest because it identifies the impact of arm and leg movements while walking, and the energy (intensity) by which a person performs these activities. The high-energy band mostly captures the fluctuations in the CSI, which are caused by movements of the person that are much faster in time. The frequency-domain features listed in Table I are calculated for all three bands described above, while the time-domain features are only calculated for the activity band. These features characterize each person's walking behavior, which is used along with the step analysis to construct a complete gait-pattern profile. This gait-pattern profile comprises an "aggregate vector" that includes vectors for individual steps and a vector for the entire walk segment. The system also includes one additional statistic for each person in the gait-pattern profile, which is the number of steps per second captured by the CSI. This statistic represents the walking speed of each person. FIG. 8B shows the effectiveness of the frequency-domain features applied to the three frequency bands. It plots energy in the low-energy band along with the mean of the DC component to show that such features can distinguish different people based on the pattern of their walking segment.

Person Identification Using CSI-Based Gait Analysis

After calculating step-based features and walk-segment features, the system combines them to build an aggregate vector representing the complete gait-pattern profile for a person. Note that in order to reduce the computation in situations where the walking segment is long, the system only considers the first few steps for the step analysis.

Next, the system uses a decision-tree machine-learning classifier to classify people based on their gait-pattern profile vectors. For example, the system can use the "random decision forests" technique to classify people. Note that the procedure to train the classifier requires the same set of features as for the testing phase. During the training phase, a person walks on a pre-determined straight line path a certain number of times. The resulting CSI data is collected and associated features are calculated. The process is repeated for all the people who would like to be identified in the smart space. As mentioned above, the person-identification classifier is specific to a given room in a home or an office. This is because changing the room and location of WiFi endpoints changes the observed multipath, which in turn affects how a person's step is observed through CSI. However, because the locations of WiFi endpoints do not change in a smart space once they are deployed, the classifier is only required to be trained once for a given location for all people. Note that machine-learning techniques other than a decision-tree machine-learning technique can also be used by the system.

Person-Identification Process

Figure 9:
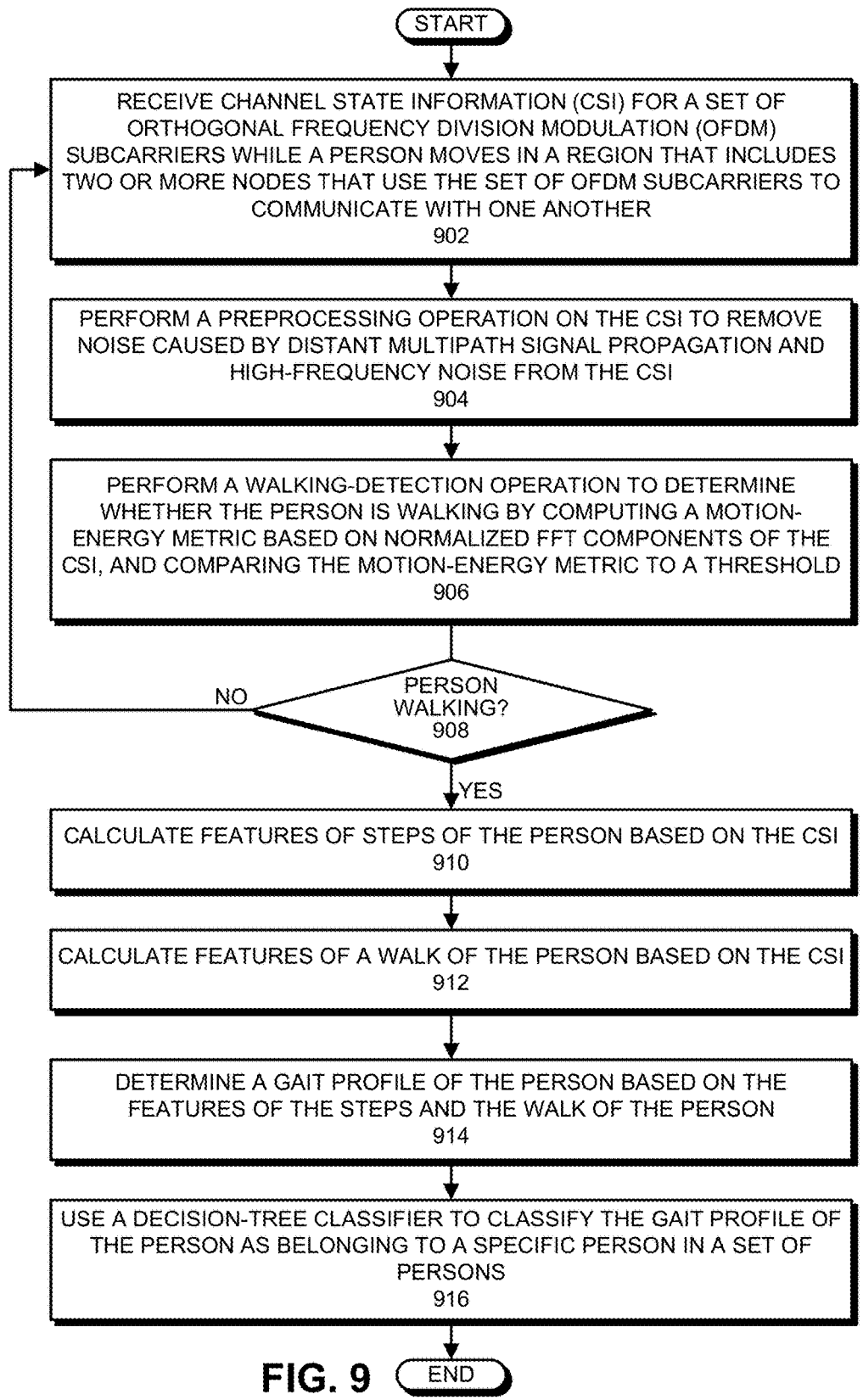
FIG. 9 presents a flow chart illustrating operations performed during the person-identification process in accordance with the disclosed embodiments.

FIG. 9 presents a flow chart illustrating operations performed during the person-identification process in accordance with the disclosed embodiments. First, the system receives CSI for a set of OFDM subcarriers while a person moves in a region that includes two or more nodes that use the set of OFDM subcarriers to communicate with one another (step 902). Next, the system performs a preprocessing operation on the CSI to remove noise caused by distant multipath signal propagation and high-frequency noise from the CSI (step 904). The system then performs a walking-detection operation to determine whether the person is walking by computing a motion-energy metric based on normalized FFT components of the CSI, and comparing the motion-energy metric to a threshold (step 906).

If a person is not walking (NO at step 908), the system returns to step 902 to receive more CSI data. On the other hand, if a person is walking (YES at step 908), the system performs a gait-analysis operation. This gait-analysis operation involves: calculating features of steps of the person based on the CSI (step 910); calculating features of a walk of the person based on the CSI (step 912); and determining a gait profile of the person based on the features of the steps and the walk of the person (step 914). Finally, the system uses a decision-tree classifier to classify the gait profile of the person as belonging to a specific person in a set of persons (step 916).

Classifier Training Process

Figure 10:
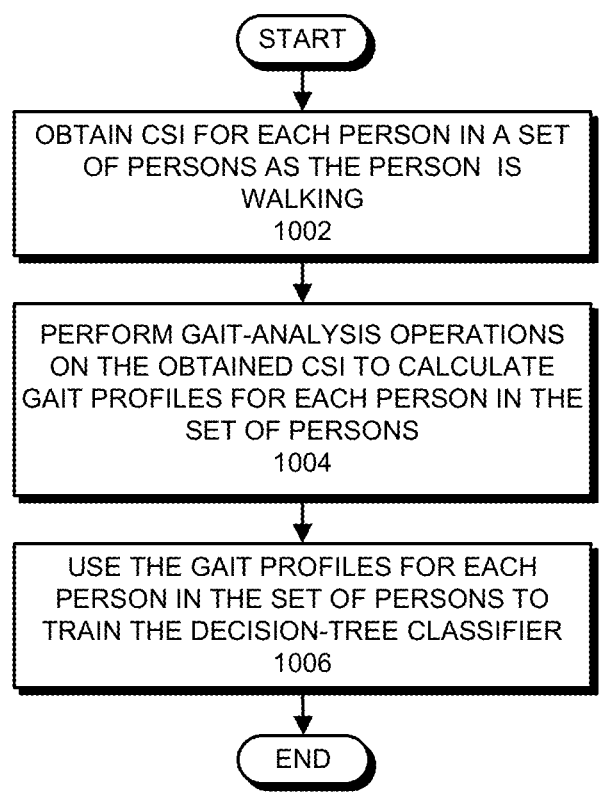
FIG. 10 presents a flow chart illustrating operations performed during the training process for a decision-tree classifier in accordance with the disclosed embodiments.

FIG. 10 presents a flow chart illustrating operations performed during the training process for a decision-tree classifier in accordance with the disclosed embodiments. First, the system obtains CSI for each person in a set of persons as the person is walking (step 1002). Next, the system performs gait-analysis operations on the obtained CSI to calculate gait profiles for each person in the set of persons (step 1004). Finally, the system performs a training operation, which involves using the gait profiles for each person in the set of persons to train the decision-tree classifier (step 1006).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for identifying a person, comprising:
   receiving channel state information (CSI) for a set of orthogonal frequency division modulation (OFDM) subcarriers while the person moves in a region that includes two or more nodes that use the set of OFDM subcarriers to communicate with one another;
   analyzing the CSI to obtain an analysis result that comprises a gait profile of the person; and
   determining the identity of the person based on the analysis result.

2. The method of claim 1, wherein the CSI includes amplitude and phase information for each of the set of OFDM subcarriers.

3. The method of claim 1, wherein the two or more communication nodes are WiFi®-capable nodes, and wherein the CSI is defined by a WiFi standard.

4. The method of claim 1, wherein prior to analyzing the CSI, the method further comprises performing a preprocessing operation on the CSI, wherein the preprocessing operation involves:
   removing noise caused by distant multipath signal propagation; and
   removing high-frequency noise.

5. The method of claim 1, wherein analyzing the CSI involves performing a walking-detection operation to determine whether the person is walking prior to performing a gait-analysis operation, wherein the walking-detection operation involves:
   computing a motion-energy metric based on normalized Fast-Fourier Transform (FFT) components of the CSI; and
   determining whether the person is walking based on the motion-energy metric.

6. The method of claim 1, wherein analyzing the CSI comprises performing a gait-analysis operation, which involves:
   calculating one or more features of steps of the person based on the CSI;
   calculating one or more features of a walk of the person based on the CSI; and
   determining the gait profile of the person based on the one or more features of the steps of the person and the one or more features of a walk of the person.

7. The method of claim 6, wherein calculating the one or more features of the steps of the person involves:
   performing a step-cycle construction operation, which uses a peak-valley detection technique based on amplitude of the CSI to divide the CSI into step cycles;
   using a band-pass filter to remove high-frequency noise from the CSI; and
   calculating one or more time-domain features of the CSI for each step cycle.

8. The method of claim 7, wherein calculating the one or more features of the walk of the person comprises calculating features over a walk segment, which includes multiple step cycles, wherein the calculated features include:
   frequency-domain features computed across all frequency bands of the CSI; and
   time-domain features computed across an activity frequency band from 0.3 to 2 Hz of the CSI.

9. The method of claim 6, wherein determining the identity of the person based on the analysis result comprises using a decision-tree classifier to classify the gait profile of the person as belonging to a specific person in a set of persons.

10. The method of claim 9, wherein prior to receiving the CSI, the method further comprises performing a training operation, which uses a set of gait profiles for each of the set of persons to train the decision-tree classifier.

11. A non-transitory computer-readable storage medium storing instructions that when executed by a computer cause the computer to perform a method for identifying a person, the method comprising:
    receiving channel state information (CSI) for a set of orthogonal frequency division modulation (OFDM) subcarriers while the person moves in a region that includes two or more nodes that use the set of OFDM subcarriers to communicate with one another;
    analyzing the CSI to obtain an analysis result that comprises a gait profile of the person; and
    determining the identity of the person based on the analysis result.

12. The non-transitory computer-readable storage medium of claim 11, wherein the CSI includes amplitude and phase information for each of the set of OFDM subcarriers.

13. The non-transitory computer-readable storage medium of claim 11, wherein the two or more communication nodes are WiFi-capable nodes, and wherein the CSI is defined by a WiFi standard.

14. The non-transitory computer-readable storage medium of claim 11, wherein prior to analyzing the CSI, the method further comprises performing a preprocessing operation on the CSI, wherein the preprocessing operation involves:

removing noise caused by distant multipath signal propagation; and removing high-frequency noise.

15. The non-transitory computer-readable storage medium of claim 11, wherein analyzing the CSI involves performing a walking-detection operation to determine whether the person is walking prior to performing a gait-analysis operation, wherein the walking-detection operation involves:

computing a motion-energy metric based on normalized Fast-Fourier Transform (FFT) components of the CSI; and determining whether the person is walking based on the motion-energy metric.

16. The non-transitory computer-readable storage medium of claim 11, wherein analyzing the CSI comprises performing a gait-analysis operation, which involves:

calculating one or more features of steps of the person based on the CSI;

calculating one or more features of a walk of the person based on the CSI; and determining the gait profile of the person based on the one or more features of the steps of the person and the one or more features of a walk of the person.

17. The non-transitory computer-readable storage medium of claim 16, wherein calculating the one or more features of the steps of the person involves:

performing a step-cycle construction operation, which uses a peak-valley detection technique based on amplitude of the CSI to divide the CSI into step cycles;

using a band-pass filter to remove high-frequency noise from the CSI; and calculating one or more time-domain features of the CSI for each step cycle.

18. The non-transitory computer-readable storage medium of claim 17, wherein calculating the one or more features of the walk of the person comprises calculating features over a walk segment, which includes multiple step cycles, wherein the calculated features include:

frequency-domain features computed across all frequency bands of the CSI; and time-domain features computed across an activity frequency band from 0.3 to 2 Hz of the CSI.

19. The non-transitory computer-readable storage medium of claim 16, wherein determining the identity of the person based on the analysis result comprises using a decision-tree classifier to classify the gait profile of the person as belonging to a specific person in a set of persons.

20. The non-transitory computer-readable storage medium of claim 19, wherein prior to receiving the CSI, the method further comprises performing a training operation, which uses a set of gait profiles for each of the set of persons to train the decision-tree classifier.

21. A system for identifying a person, comprising:

at least one processor and at least one associated memory; and a person-identification mechanism that executes on the at least one processor, wherein during operation, the person-identification mechanism:

receives channel state information (CSI) for a set of orthogonal frequency division modulation (OFDM) subcarriers while the person moves in a region that includes two or more nodes that use the set of OFDM subcarriers to communicate with one another;

analyzes the CSI to obtain an analysis result that comprises a gait profile of the person; and determines the identity of the person based on the analysis result.

22. The system of claim 21, wherein the CSI includes amplitude and phase information for each of the set of OFDM subcarriers.

23. The system of claim 21, wherein the two or more communication nodes are WiFi-capable nodes, and wherein the CSI is defined by a WiFi standard.

24. The system of claim 21, wherein prior to analyzing the CSI, the person-identification mechanism performs a preprocessing operation on the CSI, wherein the preprocessing operation involves:

removing noise caused by distant multipath signal propagation; and removing high-frequency noise.

25. The system of claim 21, wherein while analyzing the CSI, the person-identification mechanism performs a walking-detection operation to determine whether the person is walking prior to performing a gait-analysis operation, wherein the walking-detection operation involves:

computing a motion-energy metric based on normalized Fast-Fourier Transform (FFT) components of the CSI; and determining whether the person is walking based on the motion-energy metric.

26. The system of claim 21, wherein while analyzing the CSI, the person-identification mechanism performs a gait-analysis operation, which involves:

calculating one or more features of steps of the person based on the CSI;

calculating one or more features of a walk of the person based on the CSI; and determining the gait profile of the person based on the one or more features of the steps of the person and the one or more features of a walk of the person.

27. The system of claim 26, wherein while calculating the one or more features of the steps of the person, the person-identification mechanism:

performs a step-cycle construction operation, which uses a peak-valley detection technique based on amplitude of the CSI to divide the CSI into step cycles;

uses a band-pass filter to remove high-frequency noise from the CSI; and calculates one or more time-domain features of the CSI for each step cycle.

28. The system of claim 27, wherein while calculating the one or more features of the walk of the person, the person-identification mechanism calculates features over a walk segment, which includes multiple step cycles, wherein the calculated features include:

frequency-domain features computed across all frequency bands of the CSI; and time-domain features computed across an activity frequency band from 0.3 to 2Hz of the CSI.

29. The system of claim 26, wherein while determining the identity of the person based on the analysis result, the person-identification mechanism uses a decision-tree classifier to classify the gait profile of the person as belonging to a specific person in a set of persons.

30. The system of claim 29, wherein prior to receiving the CSI, the person-identification mechanism performs a training operation, which uses a set of gait profiles for each of the set of persons to train the decision-tree classifier.

* * * * *